(12) United States Patent
Munk

(10) Patent No.: US 7,438,689 B2
(45) Date of Patent: Oct. 21, 2008

(54) METHOD FOR ARBITRARY TWO-DIMENSIONAL SCALING OF PHONOCARDIOGRAPHIC SIGNALS

(75) Inventor: Flemming Munk, Viborg (DK)

(73) Assignee: Bang & Olufsen Medicom A/S, Struer (DK)

( * ) Notice: Subject to any disclaimer, the term of this patent is extended or adjusted under 35 U.S.C. 154(b) by 179 days.

(21) Appl. No.: 10/531,181

(22) PCT Filed: Oct. 9, 2003

(86) PCT No.: PCT/DK03/00681

§ 371 (c)(1),
(2), (4) Date: Apr. 11, 2005

(87) PCT Pub. No.: WO2004/032742

PCT Pub. Date: Apr. 22, 2004

(65) Prior Publication Data

US 2006/0155203 A1    Jul. 13, 2006

(30) Foreign Application Priority Data

Oct. 9, 2002    (DK) .............................. 2002 01522

(51) Int. Cl.
*A61B 5/02* (2006.01)
(52) U.S. Cl. .................................................. 600/528
(58) Field of Classification Search ................. 600/528, 600/508, 586, 534
See application file for complete search history.

(56) References Cited

U.S. PATENT DOCUMENTS

| | | | | |
|---|---|---|---|---|
| 3,318,303 A | * | 5/1967 | Hammacher | 600/485 |
| 3,581,735 A | * | 6/1971 | Gentner et al. | 600/528 |
| 4,378,022 A | * | 3/1983 | Suobank et al. | 600/528 |
| 4,446,873 A | * | 5/1984 | Groch et al. | 600/528 |
| 4,649,930 A | * | 3/1987 | Groch et al. | 600/508 |
| 4,967,760 A | * | 11/1990 | Bennett et al. | 600/528 |
| 5,012,815 A | * | 5/1991 | Bennett et al. | 600/528 |
| 5,036,857 A | * | 8/1991 | Semmlow et al. | 600/528 |
| 5,086,776 A | * | 2/1992 | Fowler et al. | 600/455 |
| 5,685,317 A | * | 11/1997 | Sjostrom | 600/528 |
| 5,825,895 A | * | 10/1998 | Grasfield et al. | 381/67 |
| 6,002,777 A | * | 12/1999 | Grasfield et al. | 381/67 |
| 6,665,564 B2 | * | 12/2003 | Lincoln et al. | 607/17 |
| 2002/0173826 A1 | * | 11/2002 | Lincoln et al. | 607/9 |
| 2004/0138572 A1 | * | 7/2004 | Thiagarajan | 600/508 |

* cited by examiner

*Primary Examiner*—Carl H. Layno
*Assistant Examiner*—Jon-Eric C Morales
(74) *Attorney, Agent, or Firm*—David S. Safran

(57) ABSTRACT

A heart signal comprising both first and second heart sounds and murmurs occurring due to various heart conditions is modeled by a sum of sinusoids automatically selected to represent the heart sound without a noise component. In an analysis step the signal parameters are measured, in an interpolation and transformation part Ω(t) and A(t) are interpolated from one window position to the next window position, and a synthesis part reconstructs the transformed heart signal. The transformations are transformations in either time scale (with unchanged frequency content) or frequency scale (with unchanged time progression), or both. Furthermore a dynamic transformation of an arbitrary heart signal to a fixed number of beats per minute is made possible.

7 Claims, 6 Drawing Sheets

METHOD FOR ARBITRARY TWO-DIMENSIONAL SCALING OF PHONOCARDIOGRAPHIC SIGNALS

Figure 1:
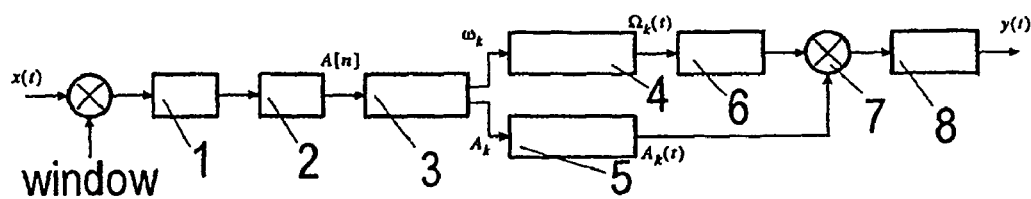

The invention relates to a method for assisting medically trained persons in diagnosing and classifying medical conditions of the heart by means of auscultation. It also relates to a method and apparatus for transforming the information content of a phonocardiographic signal to a frequency range and duration commensurate with a communication channel having properties that fall outside the normal frequency range of phonocardiographic signals.

Signals obtained by means of a transducer are phonocardiographic representations of sounds traditionally listened to by means of a stethoscope. Training in auscultation takes a long time and requires an aptitude for recognising and classifying aural cues, frequently in a noisy environment. 20-30 different conditions may need to be differentiated, and within each, the severity evaluated. Furthermore, there may be combinations among these. These factors contribute to explaining why not all physicians perform equally well when diagnosing heart conditions, and why it may be time-consuming.

Use of modern signal processing has been proposed to enhance the relevant aural cues, and in some cases it has been demonstrated that a transposition into a different frequency range or repetition of a repetitive signal at a different repetition frequency from that originally recorded may be advantageous. Among the patents that describe this kind of signal processing the following may be mentioned:

U.S. Pat. No. 4,220,160 uses the heart sound picked up by a microphone to modulate a higher and more audible carrier frequency. U.S. Pat. No. 4,424,815 is a very fundamental patent employing a range of solutions, from magnetic drum (i.e. a non-digital procedure) to a tapped delay line for stretching time while conserving frequency content. U.S. Pat. No. 4,528,689 describes a time stretching digital stethoscope that records several cycles, and obtains a "slow-down factor" proportional to the number of cycles recorded. Each part of a sound between zero crossings is repeated with opposite polarity, thereby obtaining a signal that sounds like original signals but lasting longer. Only whole-number factors are possible. U.S. Pat. No. 4,792,145 describes how frequency scaling is obtained by multiplying each Fourier spectral component by a factor. The original relationship between frequency components is retained, and it is purported that the audibility is improved. Similarly, the time may be scaled.

All of the above solutions have severe limitations, either because of an increase in non-linear distortion and noise, or because the factor for stretching can only be whole-numbered.

It has been proposed to use an algorithm based on Matching Pursuit, such as in Xuan Zhang et al. "Time-Frequency scaling transformation of the phonocardiogram based on the matching pursuit method", IEEE Trans. Biom. Eng. Vol. 45, No. 8, pp. 972-979 in view of Xuan Zhang et al. "Analysis-synthesis of the phonocardiogram based on the matching pursuit method", idem pp. 962-971 (August 1998). However, this procedure is an iterative algorithm that relies on the modulation of the signal as a sum of functions selected from a library of functions that has to be searched several times for each signal segment. It is hence a very time-consuming procedure, and in practice the control over the individual phases of the segments required for the stability of the scaled signal is questionable.

According to the invention, these disadvantages may be avoided by synthesizing a "clean" signal consisting of a sum of sinusoids and to perform a transformation on these sinusoids in order that the relative amplitudes are maintained while the frequency range or time axis are changed in a continuous range of scales. In a further refinement of this method, the scale may be linked to other phenomena by means of an auto-scale function.

An embodiment is particular in that that the signals are converted on a running basis to a sinusoidal model representation, that a time and/or frequency axis scaling is defined and used to control the amplitudes and phases of the sinusoids, which are subsequently added to create a time and/or frequency scaled representation of the phonocardiographic signal. The basis of the invention is the method in which a correct amplitude and phase adjustment of the contributing sine generators is obtained.

An advantageous embodiment of the invention is particular in that it comprises the steps of obtaining the frequency content of the signal by applying a Short Time Fourier Transform with overlapping segments, a Discrete Fourier Transform being performed on each segment, performing a frequency peak search on each segment by consecutive removal of the spectral components having the highest energy content, identifying each peak by its frequency value repeating the peak search, until a maximum number of peaks have been identified or until the energy content of the last peak is below a preset minimum, establishing a segment-by-segment map of spectral peaks, said peaks forming a track over time, optionally subjecting the frequency values of the spectral peaks to a multiplication, defining a synthesis frame of time, based on said segments, optionally subjecting each frame to a multiplication of the time scale, adjusting the phase of sine generators centered on the frequencies of the tracks, adjusting the amplitudes of said sine generators, and summing the outputs of all sine generators active at any one instant for a given frame length T.

A more general embodiment is particular in that it includes the following steps: obtaining the frequency content of the signal by applying a Short Time Fourier Transform with overlapping segments, a Discrete Fourier Transform being performed on each segment, performing a frequency peak search on each segment by repeated removal of the highest spectral "hills" identifying each peak by its frequency value, repeating the peak search until a maximum number of peaks have been identified or until the peak level of the last peak is below a preset minimum, establishing a segment-by-segment map of spectral peaks, said peaks forming a track over time, adjusting the phase of sine generators centered on the frequencies represented by the tracks, summing the outputs of all sine generators active at any one instant for a given frame length T, creating a continuous output signal by joining consecutive frames. In the present embodiment use is made of the fact that the estimate of the importance of a peak (a "hill") may be obtained by other means than an energy measure, i.e. a different sorting criterion.

A further advantageous embodiment for scaling a phonocardiographic signal on the frequency axis is particular in that the spectral peaks are multiplied by a factor q.

A further advantageous embodiment for scaling a phonocardiographic signal on the time axis by a desired factor is particular in that the frame length is multiplied by a factor p.

A further advantageous embodiment for autoscaling a phonocardiographic signal on the time axis is particular in that the scaling factor p is set such that the frame length multiplying factor is equal to the heart rate divided by 60. This means that a stability of the signal will be obtained irrespective of changes in the heart rate.

An advantageous embodiment of the invention that ensures sufficient resolution and precision in synthesis is particular in that the number of sine generators is maximum 50 in any one frame.

The invention also relates to an apparatus for performing the method, being particular in comprising means for windowing the time function, short time Fourier spectrum analysis means, means for searching and classifying spectral peaks, means for comparing phases of signals corresponding to said spectral peaks, means for controlling the phases of sine generators providing signals corresponding to said spectral peaks, means for controlling the amplitudes of said sine generators, and means for summing the signals of said controlled sine generators in order to obtain a synthesized and essentially noise free output signal representative of said time function.

Figure 2:
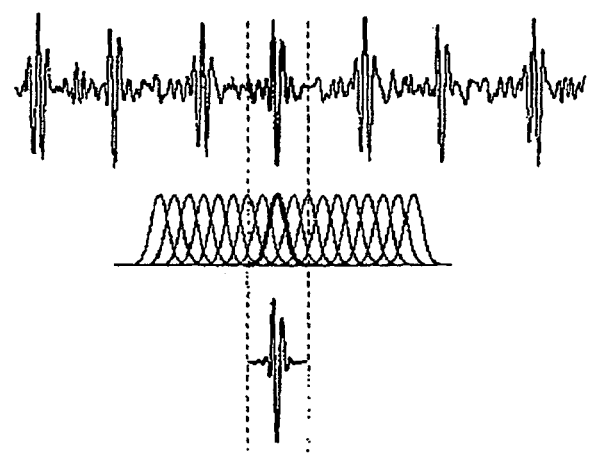
Figure 3:
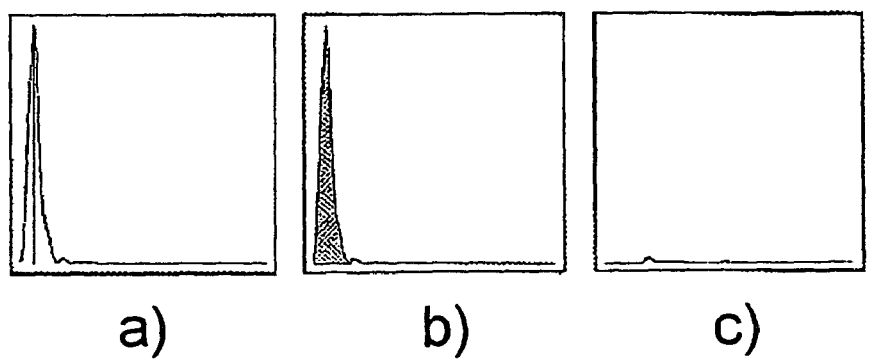
Figure 4:
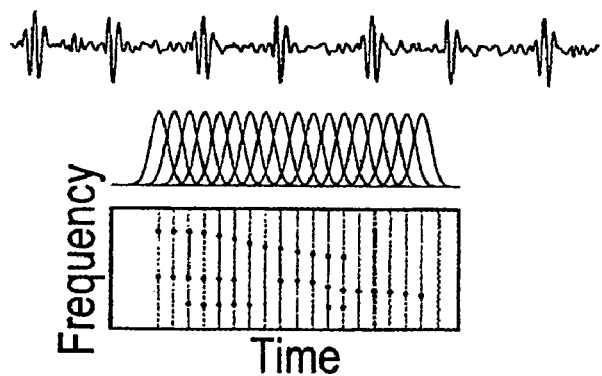
Figure 5:
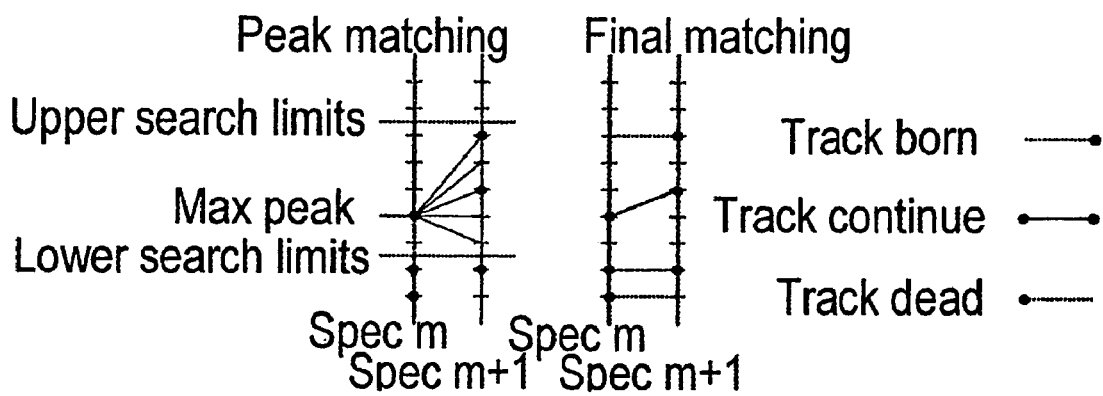
Figure 6:
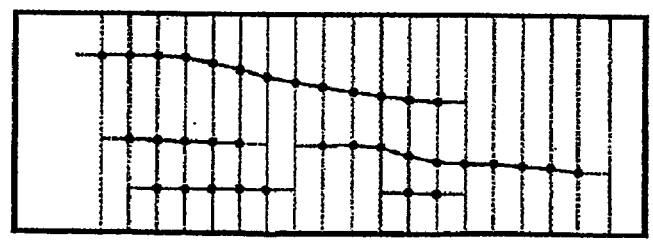
Figure 7:
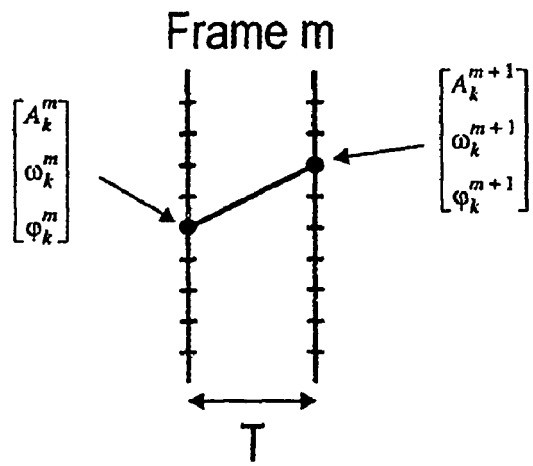
Figure 8:
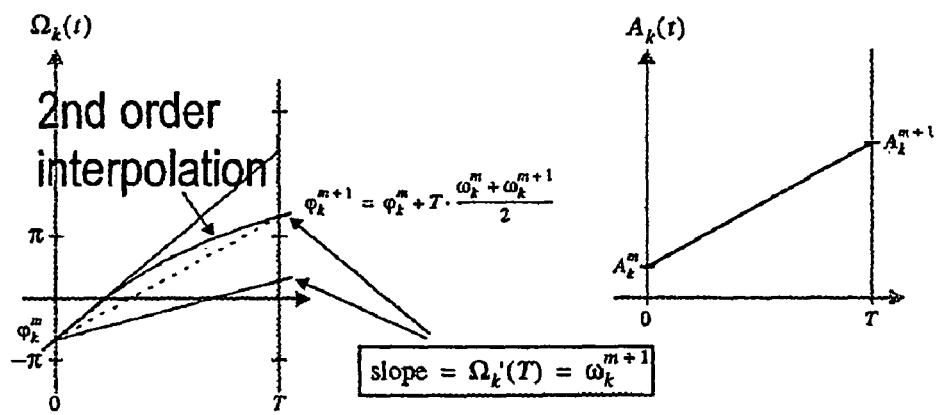
Figure 12:
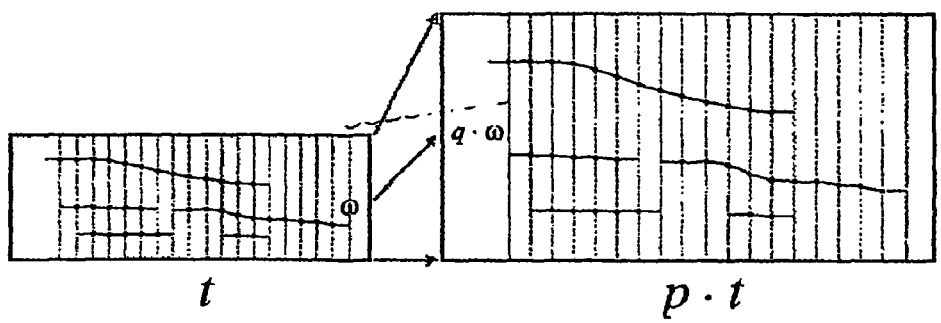
Figure 9:
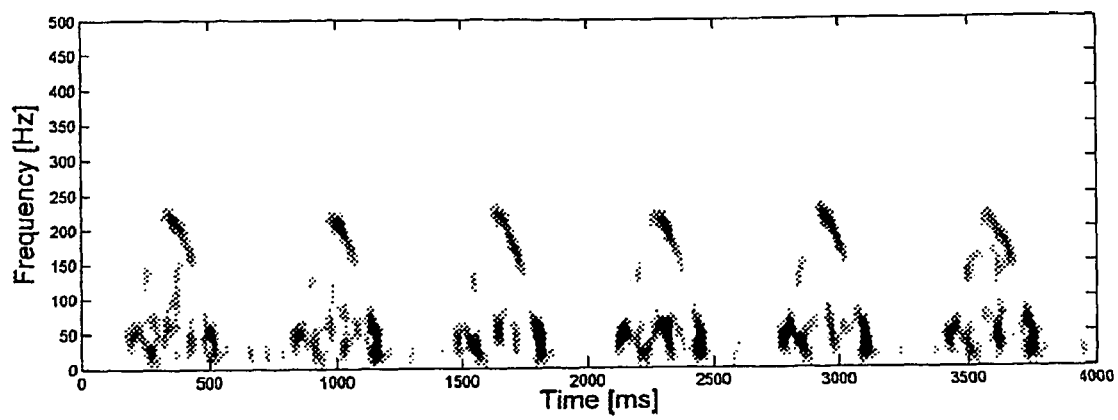
Figure 10:
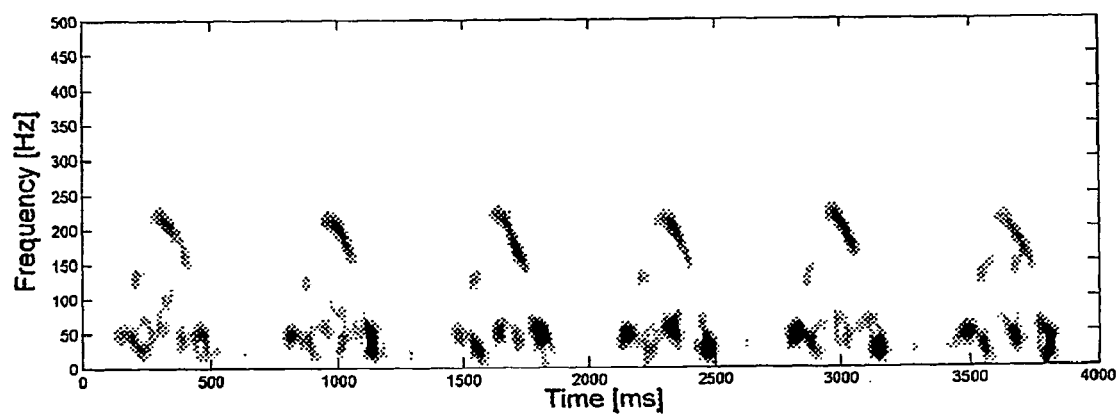
Figure 11:
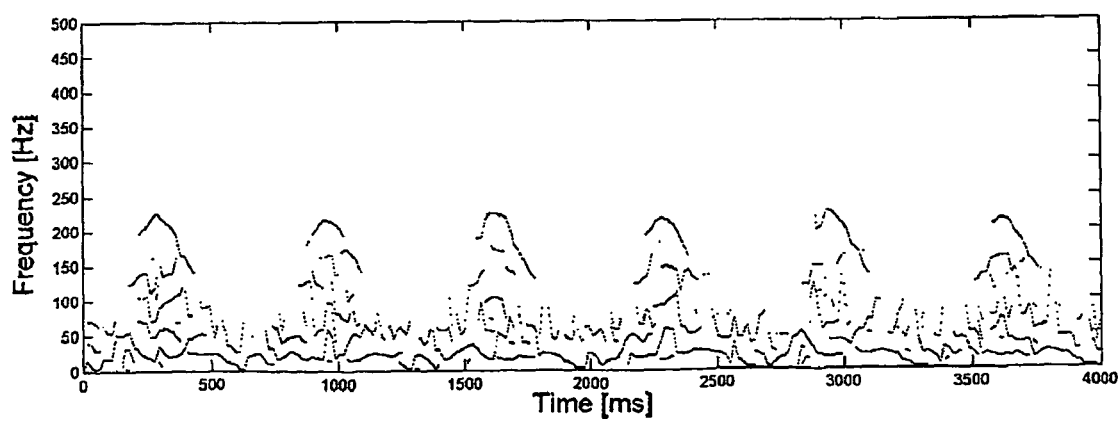
Figure 13:
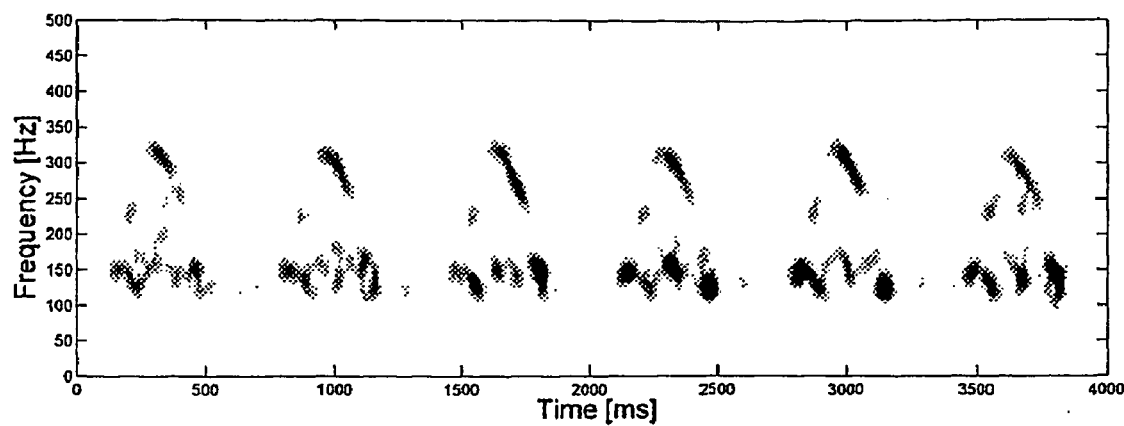
Figure 14:
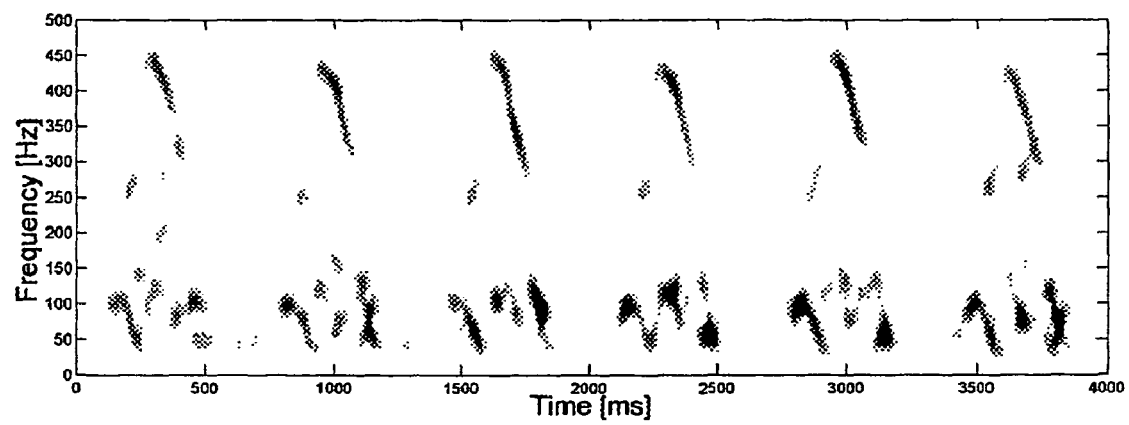
Figure 15:
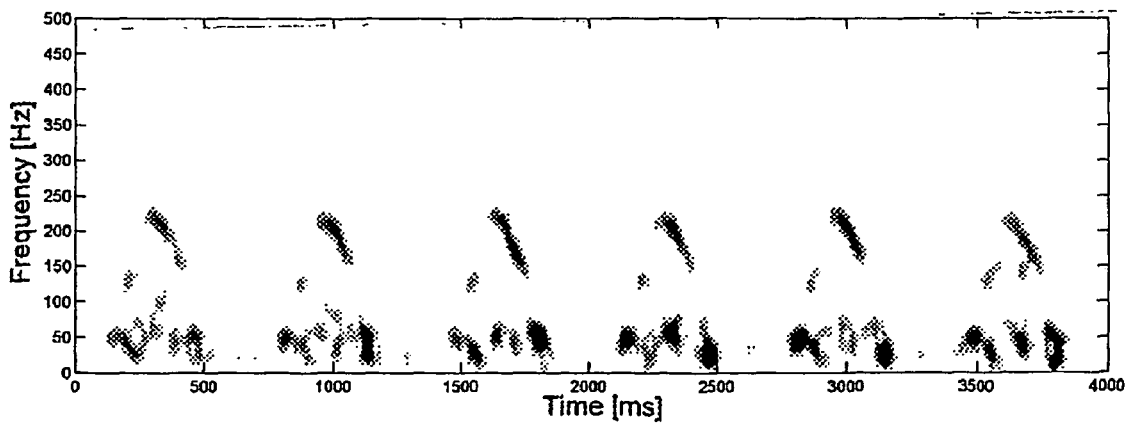
Figure 16:
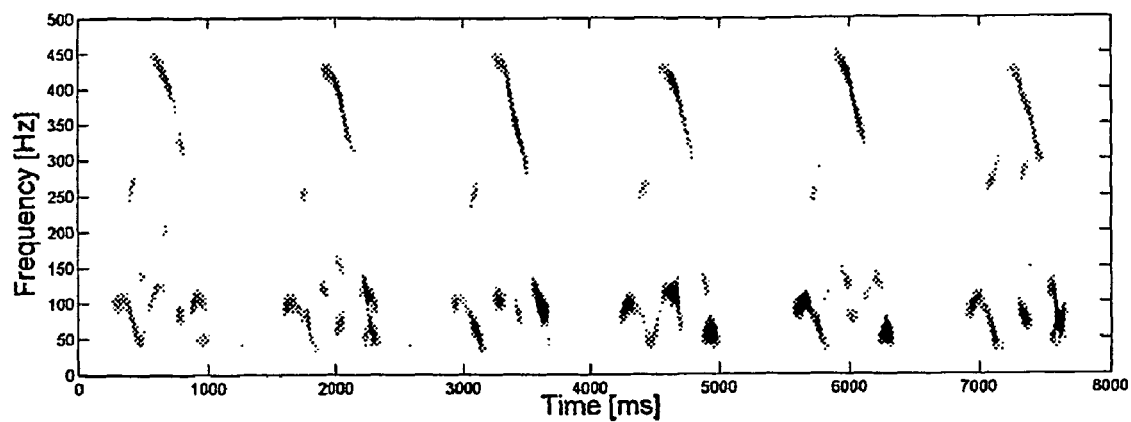
Figure 17:
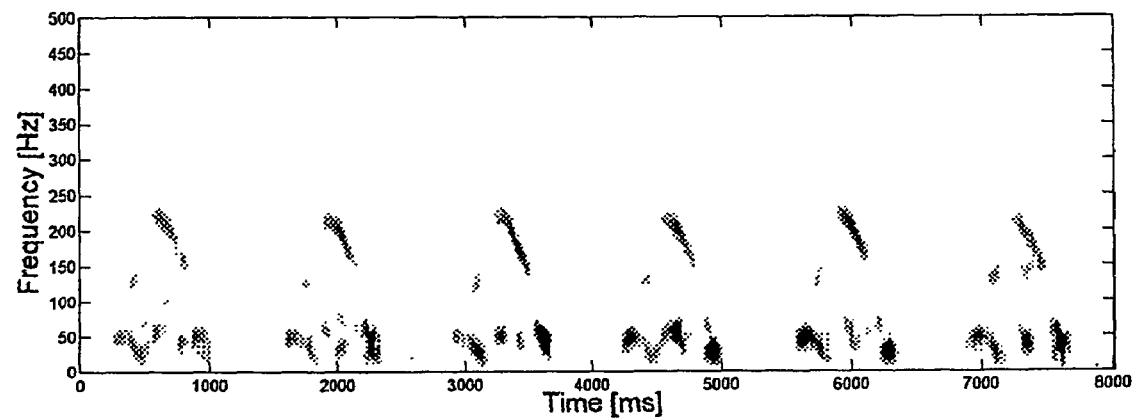
Figure 18:
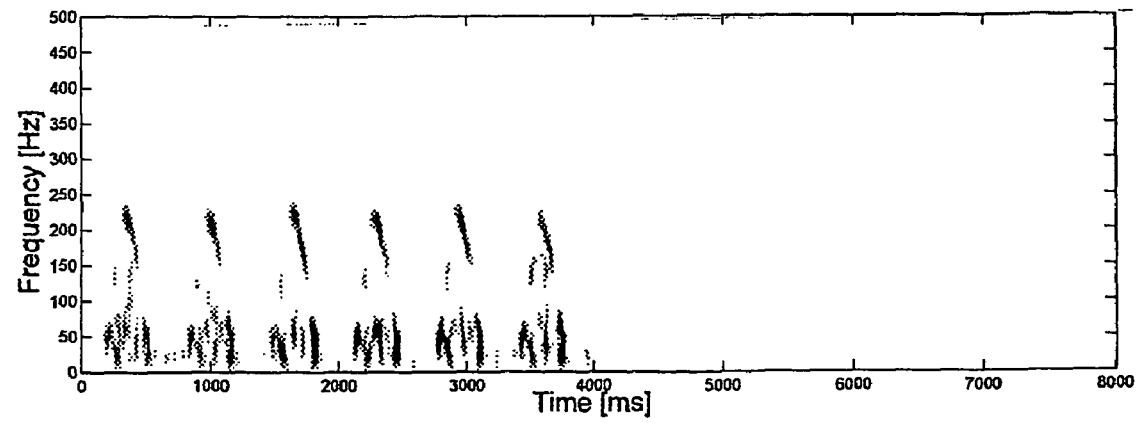

The invention will be more fully described in the following with reference to the drawing, in which FIG. 1 shows a block diagram representative of the operations performed on an input signal in order that a sinusoidal model is obtained for the signal, which is summed to obtain an output signal, FIG. 2 shows the procedure of block segmentation, FIG. 3 shows the estimation of a finite number of spectral peaks, FIG. 4 shows results of the peaks search FIG. 5 shows the matching procedure FIG. 6 shows the final results of the peak matching FIG. 7 shows boundary condition for the interpolation functions, FIG. 8 shows interpolation of instantaneous phase function and amplitude function FIG. 9 shows a spectrogram of the original heart sound, FIG. 10 shows a spectrogram of the sinusoidal coded heart sound, FIG. 11 shows a tracking pattern for the sinusoidal coded heart sound, FIG. 12 shows a Time-Frequency scaling procedure, FIG. 13 shows a spectrogram of a frequency shifted heart sound (p=1,q=1,r=100 Hz), FIG. 14 shows a spectrogram of a frequency scaled heart sound (p=1,q=2,r=0), FIG. 15 shows a spectrogram of a non-scaled sinusoidal coded heart sound (p=1,q=1,r=0), FIG. 16 shows a spectrogram of a joint time-frequency scaled heart sound (p=2,q=2, r=0), FIG. 17 shows a spectrogram of a time scaled heart sound (p=2,q=1,r=0), and FIG. 18 shows a spectrogram of the original heart sound (p=1,q=1,r=0), but using a different time axis.

The mathematical foundation for this procedure is described in the following paragraphs.

The sinusoidal model was originally developed for speech applications by McAulay and Quatieri and a thorough description can be found in Robert J. McAulay and Thomas F. Quatieri, "Speech Analysis/Synthesis Based On A Sinusoidal Representation", IEEE Transactions on Acoustics, Speech, and Signal Processing, Vol. ASSP-34, NO. 4, August 1986, page 744-754, and Thomas F. Quatieri and Robert J. McAulay, "Speech Transformations Based On A Sinusoidal Representation", IEEE Transactions on Acoustics, Speech, and Signal Processing, Vol. ASSP-34, NO. 6, December 1986, page 1449-1464. Because the spectral structure of a speech signal and a heart signal are very different (a heart beat does not have pitch like voiced speech, nor a broadband structure like unvoiced speech), the original sinusoidal model will not be able to model a heart beat properly. A sinusoidal model specific for heart sounds is developed by exploring the spectral characteristics of the heart beat, when tracking spectral components in the signal.

The sinusoidal model is based upon sinus functions. The synthesis part of the model consists in adding a group of sinusoidal functions:

$$y(t) = \sum_{k=1}^{L(t)} A_k(t)\cos(\Omega_k(t)) \quad \text{Eq. (1)}$$

The number of functions L(t) will change as a function of time, depending on the complexity of the signal. Each sinusoidal function (frequency track) is controlled by the total phase function $\Omega(t)$, and the amplitude A(t). The main objectives of the analysis part of the model is to establish the content of these two functions.

A fundamental relation for the sinusoidal model is the relationship between total phase and the instantaneous frequency:

$$\omega(t) = \frac{d}{dt}\Omega(t) \quad [\text{rad/s}] \quad \text{Eq. (2)}$$

$$\Omega(t) = \int_{-\infty}^{t} \omega(\tau)d\tau + \varphi_{offset} \quad [\text{rad}]$$

Substituting the expression for the total phase into eq. (1), the final expression for the sinusoidal model is obtained:

$$y(t) = \sum_{k=1}^{L(t)} A_k(t)\cos\left(\int_{-\infty}^{t} \omega_k(\tau)d\tau + \varphi_k\right) \quad \text{Eq. (3)}$$

The structure of a traditional sinusoidal model is illustrated in FIG. 1. The input signal x(t) is obtained from a sensor for heart sounds placed in contact with the body under examination. The output signal y(t) is made available to the medically trained person via e.g. headphones after suitable amplification. Furthermore it may be used for a visual display and comparison of frequency spectra on a display screen.

The model may be divided into three parts: an Analysis part where the signal parameters are measured, an Interpolation and transformation part, where $\Omega(t)$ and A(t) are interpolated from one window position to the next window position, and a Synthesis part where the transformed heart signal is reconstructed.

The apparatus, the principle of which is shown in FIG. 1, essentially comprises means for windowing the time function, short time Fourier spectrum analysis means 1, means for searching and classifying spectral peaks 2, 3, means 4 for comparing phases of signals corresponding to said spectral peaks, means for controlling the phases of sine generators 6 providing signals corresponding to said spectral peaks, means 5, 7 for controlling the amplitudes of said sine generators, and means 8 for summing the signals of said controlled sine generators in order to obtain a synthesized and essentially noise free output signal representative of said time function. The content of each block of FIG. 1 will be elaborated more in the following sections.

The first step of the Analysis is to measure the frequency content of the signal. As the frequency content is changing as a function of time, a Short Time Fourier Transform (STFT) is used to track the frequency content. The STFT segments the signal into overlapping segments (75%), and each segment is Fourier transformed using a Discrete Fourier Transform (DFT). The segmentation procedure is illustrated in FIG. 2.

When a signal segment has been Fourier transformed, the most dominant frequency component in the spectrum has to be found, and used as local "check points" for a frequency track over time. The original sinusoidal model finds every peak in the spectrum, and associates a sinusoidal generator to each peak. In the case of a voiced speech signal, the signal is periodic and the corresponding spectrum will be discrete (pitch). As the spectrum is discrete, the known peak search procedure will find a large number of peaks. However, a heart beat is non-periodic and has a nature like a Gaussian function modulated by a low-frequency sinusoid. The corresponding spectrum is also Gaussian, and the known peak search procedure will model this heart beat by only one sinusoidal function, where the amplitude is equal to the peak level. This will not model the heart beat correctly, compared to the remaining spectrum. However, if the amplitude of the sinusoidal function instead is set equal to the area below the curve defining the "hill" corresponding to the peak, the heart beat will be properly modelled. The peak searching procedure is illustrated in FIG. 3.

First the index for the maximum peak is found, FIG. 3a. Secondly, the area of the "hill" is estimated, FIG. 3b, and the complete "hill" is deleted from the spectrum, FIG. 3c. The procedure is repeated with the modified spectrum, until a maximum number of peaks has been found, or the peak level is below a pre-defined threshold. For certain heart sounds as many as 50 peaks corresponding to 50 sinusoids may be found.

The result from the peak search is a table of peaks for each position of the window function. The table corresponding to window position m will be termed spec m. The distance between each window position is T seconds. This is illustrated in FIG. 4.

The peaks in spec m now have to be matched together with peaks in spec m+1, in order to construct a frequency track that the total phase function $\Omega(t)$ must follow. Many different solutions for this matching problem have been proposed in the literature, as no optimal solution exits. The matching strategy used in the present invention is based on the following three rules:

high energy peaks are matched first tracks are not allowed to cross.

the frequency differences between two matched peaks must be below certain limits.

First, the procedure finds the maximum peak in spec m. This peak has to be matched with a peak in spec m+1. For this purpose, the procedure searches spec m+1 for the maximum peak within lower and upper limits. These limits are controlled by two factors. The distance to the nearest peak in spec m and the maximum allowed frequency change during T seconds. Before a match is accepted, it must be verified, i.e. it must not cross a previously found match. When the final match is verified, the two peaks are no longer visible to the matching procedure. Unmatched peaks in spec m are declared dead, and unmatched peaks in spec m+1 are declared born. The procedure is illustrated in FIG. 5, and an example of the matching process is illustrated in FIG. 6.

The synthesis will be designed for T seconds at a time, that is from window position m to window position m+1, and this T second reconstructed signal will be termed frame m, with a frame length T. The number of born, continued, and dead tracks in frame m will be termed L1(m), L2(m), and L3(m).

For each frame m, the born, continued and dead tracks are synthesized separately and added to form the final signal:

$$y^m(t) = y_1^m(t) + y_2^m(t) + y_3^m(t) \qquad \text{Eq. (4)}$$

$$= \sum_{k1=1}^{L1(m)} A_{k1}^m(t)\cos(\Omega_{k1}^m(t)) + \sum_{k2=1}^{L2(m)} A_{k2}^m(t)\cos(\Omega_{k2}^m(t)) + \sum_{k=1}^{L3(m)} A_{k3}^m(t)\cos(\Omega_{k3}^m(t))$$

Each track k in frame m has to be synthesised by a sinusoidal function $A_k(t)\cos(\Omega_k(t))$. The track is up to now only specified by the start and end points. This is illustrated in FIG. 7.

$A^m_k$ is the amplitude of the Fourier coefficients, $\omega^m_k$ is the frequency of the Fourier coefficient and $\phi^m_k$ is the phase offset for the current track. The phase offset is increased by an average phase step dependent on the start and stop frequency of the track (see FIG. 8). The original model is based on the phase of the Fourier coefficients. The amplitude is interpolated by $A_k(t)$, and the instantaneous phase is interpolated by $\Omega_k(t)$. The interpolation functions are only constrained by the start and stop conditions:

$$A_k(0) = A_k^m \qquad A_k(T) = A_k^{m+1} \qquad \text{Eq. (5)}$$

$$\Omega_k(0) = \varphi_k^m \qquad \Omega_k(T) = \varphi_k^m + T \cdot \frac{\omega_k^m + \omega_k^{m+1}}{2}$$

$$\Omega_k'(0) = \omega_k^m \qquad \Omega_k'(T) = \omega_k^{m+1}$$

The amplitude function is not critical, so a linear interpolation function will be used for $A_k(t)$. However, the instantaneous phase function $\Omega_k(t)$ is more critical because any discontinuity in the phase progress will deteriorate the perceptual quality of the final sound. In the following, the synthesis of born, continued, and dead tracks will be designed separately.

In the case of a continued track, a second order polynomial will be used to interpolate a smooth phase progress during a frame:

$$\Omega(t) = a_1 + a_2 \cdot t + a_3 t^2 \qquad \text{Eq. (6):}$$

This is illustrated in FIG. 8.

The coefficients are determined by inserting the conditions from Eq. (5) into Eq. (6):

$$\Omega(0) = a_1 = \varphi_k^m \qquad \text{Eq. (7)}$$

$$\Omega'(0) = a_2 = \omega_k^m$$

$$\Omega(T) = a_1 + a_2 \cdot T + a_3 \cdot T^2$$

$$= \varphi_k^m + T \cdot \frac{\omega_k^m + \omega_k^{m+1}}{2} \Rightarrow a_3$$

$$= \frac{\omega_k^{m+1} - \omega_k^m}{2T}$$

The linear interpolation of the amplitude function is achieved by:

$$A_k^m(t) = A_k^m - t \cdot \frac{A_k^m - A_k^{m+1}}{T} \qquad \text{Eq. (8)}$$

The final equations for the synthesis of a continued track k in frame m is given by:

Continued Track $$\Omega_k^m(t) = \varphi_k^m + \omega_k^m \cdot t + \frac{\omega_k^{m+1} - \omega_k^m}{2T} \cdot t^2 \qquad \text{Eq. (9)}$$

$$A_k^m(t) = A_k^m - t \cdot \frac{A_k^m - A_k^{m+1}}{T}$$

Two special cases remain to be considered. When a track is declared dead or born, we do not have both start and end conditions for them.

In the case of a born track, an instantaneous phase function will be initiated from the begining of frame k, with $A^m_k=0$, $\omega^m_k = \omega^{m+1}_k$, $\phi^{m+1}_k=0$, and the second order instantaneous phase function is reduced to a linear function:

Born Track:

$$\Omega_k^m(t) = t \cdot \omega_k^{m+1} \qquad \text{Eq. (10)}$$

$$A_k^m(t) = t \cdot \frac{A_k^{m+1}}{T}$$

When a track is declared dead, the track is terminated at the end of frame m using $A^{m+1}_k=0$, $\omega^{m+1}_k=\omega^m_k$, and $\phi^{m+1}_k=T\cdot\phi^m_k$, and the second order instantaneous phase function is again reduced to a linear function:

Dead Track:

$$\Omega_k^m(t) = t \cdot \omega_k^m + \varphi_k^m \qquad \text{Eq. (11)}$$

$$A_k^m(t) = \frac{A_k^m}{T}(T - t)$$

In order to explain more fully the sinusoidal model according to the invention it is prepared for implementation in a mathematical simulation program, such as MatLab (™), and the interpolation functions are hence converted to discrete index. The discrete time version is obtained using the following substitutions:

$$t = n \cdot \Delta \qquad \text{Eq. (12)}$$

$$T = N \cdot \Delta$$

$$\omega_k^m = \frac{v_k^m}{N_{DFT}} \cdot \frac{2\pi}{\Delta}$$

These substitutions are now inserted into the main equations for the sinusoidal model.

$$\Omega_k^m[n] = \Omega_k^m(n\Delta) \qquad \text{Eq. (13)}$$

-continued $$= a_1 + a_2 n\Delta + a_3 n^2 \Delta^2$$

$$= \varphi_k^m + \frac{v_k^m}{N_{DFT}} \cdot \frac{2\pi}{\Delta} \cdot n\Delta +$$

$$\frac{\frac{v_k^{m+1}}{N_{DFT}} \cdot \frac{2\pi}{\Delta} - \frac{v_k^m}{N_{DFT}} \cdot \frac{2\pi}{\Delta}}{2(N \cdot \Delta)} n^2 \Delta^2$$

$$= \varphi_k^m + n \cdot v_k^m \cdot \frac{2\pi}{N_{DFT}} + n^2 \cdot (v_k^{m+1} - v_k^m) \frac{\pi}{N \cdot N_{DFT}}$$

The time index n is running from 0 to N. The discrete amplitude function is given by:

$$A_k^m[n] = A_k^m(n \cdot \Delta) \qquad \text{Eq. (14)}$$

$$= A_k^m - n \cdot \Delta \cdot \frac{A_k^m - A_k^{m+1}}{N \cdot \Delta}$$

$$= A_k^m - n \cdot \frac{A_k^m - A_k^{m+1}}{N}$$

The final equations for a discrete-time continued track is:

Discrete Continued Track:

$$\Omega_k^m[n] = \varphi_k^m + n \cdot v_k^m \cdot \frac{2\pi}{N_{DFT}} + n^2 \cdot (v_k^{m+1} - v_k^m) \frac{\pi}{N \cdot N_{DFT}} \qquad \text{Eq. (15)}$$

$$A_k^m[n] = n \cdot \Delta \cdot \frac{A_k^{m+1}}{N \cdot \Delta} = n \cdot \frac{A_k^{m+1}}{N}$$

The discrete function for a born and dead track can likewise be found following the same approach:

Discrete Born Track:

$$\Omega_k^m[n] = n \cdot \Delta \cdot \frac{v_k^{m+1}}{N_{DFT}} \cdot \frac{2\pi}{\Delta} = n \cdot v_k^{m+1} \cdot \frac{2\pi}{N_{DFT}} \qquad \text{Eq. (16)}$$

$$A_k^m[n] = n \cdot \Delta \cdot \frac{A_k^{m+1}}{N \cdot \Delta} = n \cdot \frac{A_k^{m+1}}{N}$$

Discrete Dead Track:

$$\Omega_k^m[n] = n \cdot \Delta \cdot \frac{v_k^m}{N_{DFT}} \cdot \frac{2\pi}{\Delta} + \varphi_k^m = n \cdot v_k^m \cdot \frac{2\pi}{N_{DFT}} + \varphi_k^m \qquad \text{Eq. (17)}$$

$$A_k^m[n] = \frac{A_k^m}{N \cdot \Delta}(N \cdot \Delta - n \cdot \Delta) = \frac{A_k^m}{N}(N - n)$$

The result of coding a heart sound with severe systolic murmurs is illustrated in FIGS. 9, 10, and 11. FIG. 11 shows the track pattern that is used to reconstruct the heart sound and clearly illustrates how tracks are born, are continued, and die, according to the spectral content of the original heart sound, and in this respect FIG. 11 is a practical demonstration of the principle shown in FIG. 6.

Using the novel sinusoidal model described above, we are now in a position to make modifications to the original signal, which would normally be very difficult to obtain. As the model contains a very precise description of how the frequency content of the signal is changing over time, it provides a good foundation for making signal transformations like time stretching (without changing the frequency structure), frequency stretching (without changing the time progress), and joint time frequency stretching.

The sinusoidal model may be extended to a time-frequency scaled sinusoidal model with small modifications. The joint time frequency scaling is obtained by mapping track information at time t and frequency ω in the original model to a new time position t=p·t, where p is the time scaling factor, and new frequency position ω=q·t, where q is the frequency scaling factor. A pure frequency scaled model, may be obtained by setting p=1, and a pure time scaling model may be obtain by setting q=1. The procedure is illustrated in FIG. 11.

The time scaling is implemented in the sinusoidal model by changing the frame T to p·T in the interpolation functions Ω(t) and A(t). Frequency scaling can be implemented by shifting the peaks found by the peak searching procedure from ω to q·ω:

$$\tilde{T} = p \cdot T$$

$$\tilde{\omega} = q \cdot \omega \quad \text{Eq. (18):}$$

When q·ω crosses half the sampling frequency, the track is removed. Every time a born or continued track has been synthesized, the phase offset $\phi^{m+1}_k$ has to be updated to:

$$\phi_k^{m+1} = \Omega_k^m(T) \quad \text{Eq. (19):}$$

Other frequency modifications will also be possible. Heterodyne modification is obtained by shifting peaks from ω to ω+r, where r is the amount of the spectrum movement.

The time-scaled sinusoidal model may form the foundation for a method for auto-scaling a heart sound signal, which scales arbitrary heart sounds to 60 beats per minute (bpm). This autoscaling capability is obtained using a scale factor p:

$$p = \frac{h}{60} \quad \text{Eq. (20)}$$

where h is the heart rate. Because of the sample rate in the Fourier transforms there is no problem in following a changing heart rate dynamically. The usefulness lies in the fact that a stressed heart will display a change in the spectral content of the heart sound, and focusing on this phenomenon may be simplified if the simultaneous increase in heart rate may be disregarded.

In FIGS. 13 to 18, the results of applying the above described procedure are shown when used on a heart sound.

One particular use of the procedure relates to the transmission of very low frequency signals over a channel with a limited bandwidth centered much higher than the low frequency signals, such as heart sound signals to be transmitted over a traditional telephone line with the bandwidth 300-3400 Hz. Traditionally this could be obtained by heterodyning only, in which harmonic relationships between partials are destroyed. According to the present invention scaling to the frequency range of interest will preserve such harmonic relationships.

The basic parameters that apply to the procedure described above when used with arbitrary heart sounds may obviously be chosen by the skilled person according to specific needs. However, the examples reproduced here are based on the following parameters:

| | |
|---|---|
| Sampling frequency: | 1 kHz |
| Window length: | 64 samples |
| Window shift: | 4 samples |
| Window type: | Gaussian |
| Max. number of sines: | 50 |
| Max. frequency shift of tracks between neighbouring windows: | 80 Hz |

It will be understood that once the signal has been converted to digital representation of data, its manipulation may take place in dedicated processors, RISC processors or general purpose computers, the outcome of the manipulation being solely dependent on the instructions performed on the data under the control of the program written for the processor in order to obtain the function. The physical location of the data at any one instant (i.e. in varying degrees of processing) may or may not be related to a particular block in the block diagram, but the representation of the invention in the form of interconnected functional blocks provides the skilled person with sufficient information to obtain the advantages of the invention.

The foregoing description of the specific embodiments will so fully reveal the general nature of the present invention that others skilled in the art can, by applying current knowledge, readily modify or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

The invention claimed is:

1. A method for arbitrary time and/or frequency scaling by analysis, classification and subsequent re-synthesis of phonocardiographic signals obtained from a transducer and subjected to digital spectral analysis, characterised in that the signals are converted on a running basis to a sinusoidal model representation, that a time and/or frequency axis scaling is defined and used to control the amplitudes and phases of the sinusoids, which are subsequently added to create a time and/or frequency scaled representation of the phonocardiographic signal and comprising the further steps of:

obtaining the frequency content of the signal by applying a Short Time Fourier Transform with overlapping segments, a Discrete Fourier Transform being performed on each segment, performing a frequency peak search on each segment by consecutive removal of the spectral components having the highest energy content, identifying each peak by its frequency value repeating the peak search until a maximum number of peaks have been identified or until the energy content of the last peak is below a preset minimum, establishing a segment-by-segment map of spectral peaks, said peaks forming a track over time optionally subjecting the frequency values of the spectral peaks to a multiplication defining a synthesis frame [frame m] of time, based on said segments optionally subjecting each frame to a multiplication of the time scale adjusting the phase of sine generators centered on the frequencies of the tracks adjusting the amplitudes of said sine generators summing the outputs of all sine generators active at any one instant for a given frame length T.

2. A method according to claim 1, for scaling a phonocardiographic signal on the frequency axis by a desired factor, characterised in that the spectral peaks are multiplied by a factor q.

3. A method according to claim 1, for scaling a phonocardiographic signal on the time axis by a desired factor, characterised in that the frame length is multiplied by a factor p.

4. A method according to claim 1, for autoscaling a phonocardiographic signal on the time axis, characterised in that the scaling factor p is set such that the frame length [T] multiplying factor is equal to the heart rate divided by 60.

5. A method according to claim 1, or 3, characterised in that the number of sine generators is equal to or below 50.

6. A method for arbitrary time and/or frequency scaling by analysis, classification and subsequent re-synthesis of phonocardiographic signals obtained from a transducer and subjected to digital spectral analysis, characterised in that the signals are converted on a running basis to a sinusoidal model representation, that a time and/or frequency axis scaling is defined and used to control the amplitudes and phases of the sinusoids, which are subsequently added to create a time and/or frequency scaled representation of the phonocardiographic signal and including the following steps:

obtaining the frequency content of the signal by applying a Short Time Fourier Transform with overlapping segments, a Discrete Fourier Transform being performed on each segment, performing a frequency peak search on each segment by repeated removal of the highest spectral "hills" identifying each peak by its frequency value repeating the peak search until a maximum number of peaks have been identified or until the peak level of the last peak is below a preset minimum, establishing a segment-by-segment map of spectral peaks, said peaks forming a track over time adjusting the phase of sine generators centered on the frequencies represented by the tracks summing the outputs of all sine generators active at any one instant for a given frame length T creating a continuous output signal by joining consecutive frames.

7. An apparatus for performing the method of any of the above claims on a phonocardiographic time function, characterised in that it comprises means for windowing the time function [x(t)], short time Fourier spectrum analysis means [1], means for searching and classifying spectral peaks [2, 3], means [4] for comparing phases of signals corresponding to said spectral peaks, means for controlling the phases of sine generators [6] providing signals corresponding to said spectral peaks, means [5, 7] for controlling the amplitudes of said sine generators [6], and means [8] for summing the signals of said controlled sine generators in order to obtain a synthesized and essentially noise free output signal [y(t)] representative of said time function.

* * * * *